Figure 1:
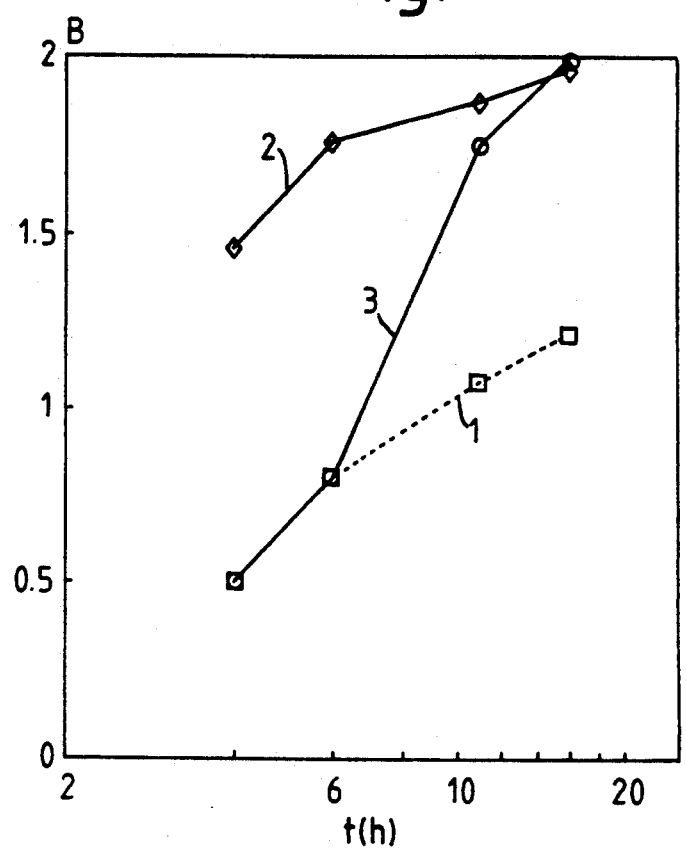

United States Patent [19]

Potman et al.

[11] Patent Number: 5,288,509
[45] Date of Patent: Feb. 22, 1994

[54] METHOD FOR THE PREPARATION OF A YEAST EXTRACT, SAID YEAST EXTRACT, ITS USE AS A FOOD FLAVOUR, AND A FOOD COMPOSIITON COMPRISING THE YEAST EXTRACT

[75] Inventors: Ronald P. Potman, Schiedam; Johannes Wesdorp, Roosendaal, both of Netherlands

[73] Assignee: Lever Brothers Company, New York, N.Y.

[21] Appl. No.: 383,337

[22] Filed: Jul. 24, 1989

[30] Foreign Application Priority Data

Jul. 22, 1988 [EP] European Pat. Off. ........ 88201596.9
Apr. 13, 1989 [EP] European Pat. Off. ........ 89200922.6

[51] Int. Cl.$^5$ .............................................. A23L 1/28
[52] U.S. Cl. .................................. 426/60; 426/62; 435/255.1; 435/259
[58] Field of Search ................................ 426/60–64, 426/534, 650, 655, 388, 549, 573, 574, 580–582, 589, 590, 600–603, 615, 641, 652, 653, 658, 660; 435/255, 256

[56] References Cited

U.S. PATENT DOCUMENTS 3,443,969 5/1969 Nakajima et al.
4,080,260 3/1978 Chao ........................................ 426/60
4,218,481 8/1980 Chao et al. ............................. 426/60
4,559,307 12/1985 Hopkins .................................. 426/60

FOREIGN PATENT DOCUMENTS 0191513 8/1986 European Pat. Off.
1262535 7/1960 France.
1071027 6/1967 United Kingdom.
8805267 7/1988 World Int. Prop. O.

OTHER PUBLICATIONS

Marukin Shoyo Co., Ltd., Chemical Abstracts, vol. 70, 1969, p. 217, abstract No. 113862w, Columbus, Ohio, U.S.

Primary Examiner—Donald E. Czaja
Assistant Examiner—Leslie Wong
Attorney, Agent, or Firm—Cushman, Darby & Cushman

[57] ABSTRACT

The invention relates to a method for the preparation of a yeast by degrading yeast with enzymes having RNA degrading activity leading to 5'-ribonucleotides, wherein oxidizing conditions are maintained during the enzymatic degradation. Preferably the proteolytic degradation is carried out under anaerobic conditions, and the RNA degrading activity leading to 5'-ribonucleotides under oxidizing conditions, such as an oxygen saturated incubation medium. The invention also relates to the yeast extract obtained, to the use of the yeast extract and to a flavouring and a food composition comprising it.

13 Claims, 2 Drawing Sheets

METHOD FOR THE PREPARATION OF A YEAST EXTRACT, SAID YEAST EXTRACT, ITS USE AS A FOOD FLAVOUR, AND A FOOD COMPOSIITON COMPRISING THE YEAST EXTRACT

The invention relates to a method for the preparation of a yeast extract by enzymatic treatment of yeast, to the yeast extract obtainable by this method, to the use of the yeast extract as a food flavour, and to food compositions comprising this yeast extract.

European patent application (EP-A) 191 513 discloses a method for the preparation of a food flavour by degrading inactivated yeast with enzymes having proteolytic activity (for instance papain) and RNA degrading activity leading to 5'-ribonucleotides (for instance phosphodiesterase), and fermentation with micro-organisms.

The RNA degradation leads to 5'-ribonucleotides, of which guanosine-5'-monophosphate (5'-GMP) contributes for the major part to the taste improvement by these nucleotides.

Furthermore German patent application (DE-A) 30 00 188 discloses the autolysis of yeast followed by inactivation and RNA-degradation by malt rootlets (phosphodiesterase) yielding a product containing 5'-GMP and free amino acids. Disadvantage of these processes is that the amount of 5'-GMP formed is suboptimal.

During further research it has been found that the 5'-ribonucleotides content of a yeast extract is dependent on the conditions of the enzymatic degradation.

Under strict anaerobic conditions enzymatic degradation of a specific inactivated yeast leads to a yield of a yeast extract of about 60%, and having a 5'-GMP content of only 1.8% by weight of the dry yeast extract (degradation time about 18 hours). However, under strict aerobic conditions the extract yield from the same yeast is only about 46% but the yeast extract contains 3.9% by weight 5'-GMP. Any yield and any 5'-GMP content between the respective limits given above are obtainable by degrading the yeast partly under oxidizing conditions. It is an object of the present invention to provide a method for the preparation of a yeast extract of which the composition and the yield are adjustable to the specific needs of the yeast extract as a food flavour in a specific food composition.

Accordingly, the present invention relates to a method for the preparation of a yeast extract by degrading yeast with enzymes having RNA degrading activity leading to 5'-ribonucleotides, wherein oxidizing conditions are maintained during that enzymatic degradation.

Preferably the yeast is degraded with endogenous and/or exogenous enzymes having proteolytic activity and RNA degrading activity leading to 5'-ribonucleotides, and the enzymatic degradation is at least partly carried out under oxidizing conditions. Typically, the present invention provides two types of yeast extract preparing methods:

a) a single-step method in which yeast directly is degraded enzymatically under oxidizing conditions, resulting in a yeast extract having a very high 5'-GMP content, and in a moderate yeast extract yield; and b) a two-step method comprising an anaerobic proteolytic degradation step using endogenous and/or exogenous enzymes and the RNA degradation step under oxidizing conditions, resulting in a yeast extract having a high 5'-GMP content and in a high yeast extract yield.

In both methods the increased 5'-GMP content is obtained without the addition of additional RNA. The two-step method combines a high yeast extract yield with an optimal RNA degradation into 5'-GMP and appears to be the most preferred method.

Preferably the yeast is first degraded by proteolytic enzymes under anaerobic conditions and subsequently subjected to the degradation by RNA degrading enzymes under oxidizing conditions, because the proteolytic enzymes, notably papain, are irreversibly inactivated under oxidizing conditions, whereas the RNA degrading enzymes, notably phosphodiesterase, are reversibly inactivated under anaerobic conditions.

The anaerobic conditions result in a better yeast extract yield, whereas the oxidizing conditions are advantageous for an improvement of the 5'-ribonucleotides content. If desired, the enzymatic degrading treatment may further comprise a fermentation, provided that a carbon source is available. This fermentation leads to the formation of organic acids like lactic acid and succinic acid which not only modify the taste of the yeast extract, but also act as a preserving agent.

Suitable yeast starting materials belong to the group consisting of Saccharomyces species, Kluyveromyces species, Candida species, Torula species, Fusarium species, Zymomonas species and Pychia species. Saccharomyces, Kluyveromyces, Candida and Torula species are preferred. More in particular, yeasts like *Saccharomyces cerevisiae, Kluyveromyces lactis, Kluyveromyces fragiles, Kluyveromyces marxianus, Candida utilis* may be used.

At some stage of the enzymatic degradation of the yeast, but certainly before the RNA degradation step, the yeast is inactivated in order to remove 5'-GMP degrading activity, e.g. by heat treatment at a temperature between 70° and 150° C. for 5 to 120 minutes. Inactivation by cooking usually requires an aqueous suspension with a dry matter content up to 30%. Inactivation is, of course, also possible by means of the addition of chemicals or by radiation.

Both one-step, or multi-step enzymatic degradation and fermentation may be carried out in any sequence or simultaneously, provided that a carbon source is available for fermentation.

The enzymatic degradation of the yeast is carried out by means of suitable enzyme preparations of bacterial, vegetable, yeast or animal origin. If part of the enzymatic degradation is done before the yeast is inactivated, the own internal enzyme activity of the yeast may also contribute to the process. Enzyme preparations used have one or more of the following activities:

1. Proteolytic activity

Preferably one or more of the following enzymes are used:

Pancreatin, Trypsin (from porcine or bovine pancreatid tissues), Bromelain (from Ananas comosus/bracteatus), Ficin, Molsin, Chymotrypsin, Papain (from Carica papaya), Chymopapain (from *Carica papaya*), Pepsin (from porcine gastric mucosa), Rennin, or proteases from *Bacillus subtilis, Aspergillus oryzae, Penicillium dupontii, Streptomyces griseus, Mucor miehei/Dusillus,* hog kidney, etc. In addition the yeasts own proteolytic enzyme system may be active during this step.

Depending on the particular enzyme used, the incubation is carried out at a pH lying between 2 and 10 and a temperature lying between 20° and 80° C. Pepsin has an optimal activity at pH 2-3, protease from *Streptomyces griseus* an optimura at pH 9-10 and papain is still active at 70°-80° C.

2. Cell wall degradation activity

Beta-glucanase may be obtained from *Bacillus subtilis/licheniformis, Penicillium emersonii, Aspergillus niger/oryzae.*

The incubation is usually carried out at a temperature lying between 20° and 70° C. and a pH of 3-7.

3. Amylase or glycogen degrading activity

Alpha- and beta-amylase, derived from *Bacillus subtilis, Aspergillus spp,* are generally used in incubations at pH 4-8 and at a temperature of 20°-70° C.

4. RNA degrading activity leading to 5'-ribonucleotides

Phosphodiesterase, e.g. obtained from malt rootlets or fungal extracts such as from *Penicillium citrinum,* may be used in incubations at pH 3-9 and at a temperature of 20°-80° C. Sometimes it is advantageous to add some PNA and/or protein before this step is carried out.

5. Lipolytic activity

Pancreatin or pancreatic lipase may be used, and are incubated at pH 5-10 and at a temperature between 20° and 70° C.

6. Deaminase activity

Deaminase e.g. derived from *Aspergillus spp.* may be used in incubations at a pH between 3 and 8 and at a temperature between 30° and 60° C.

The enzymatic degradation step of the present invention usually combines several of these enzymatic activities. This can be achieved by simultaneous incubation with a number of enzymes. Also a plurality of incubations with different enzymes are possible, often under different conditions of pH and temperature.

There are, of course, a number of enzyme preparations which are commercially available, which combine several enzymatic activities, such as pancreatin, etc. When a plurality of enzymatic activities are used, the incubation may lead to the formation of amino acids, peptides, mono- and disaccharides, 5'-ribonucleotides and fatty acids.

It is preferred to use such a plurality of enzymes, either simultaneously or consecutively, having at least proteolytic activity and RNA degrading activity.

If oxidizing conditions are maintained using oxygen ($O_2$), it is preferred to monitor the oxygen content of the incubation medium during RNA degradation. Thus, it is possible to replenish oxygen consumed by the incubation medium if necessary. Preferably the oxygen concentration should be maintained at 0.1-30 mg/l. Oxygen may be added as such or in a gas mixture such as air. Alternatively, oxidative conditions may be achieved using a peroxide, such as hydrogen peroxide.

In accordance with one preferred embodiment of the invention the enzymatic degradation is used in conjunction with fermentation with micro-organisms. Preferably enzymatic degradation is followed by fermentation so that saccharides are converted inter alia into organic acids like lactic acid, succinic acid, etc. It is also advantageous to carry out enzymatic degradation simultaneously with fermentation.

Fermentation by micro-organisms is usually carried out at a pH from 4.5 to 7.5 and at a temperature of 20°-65° C., for a period ranging between 4 hours and 14 days. Under practical conditions of the present invention, microorganisms are added which are generally used in the preparation of milk products, meat and meat products, fermented vegetables, fermented beverages, bread, pickles and sauces, such as: Lactic acid bacteria, e.g. *Lactobacillus acidophilus, L. delbrueckli, L. casei, L. plantarum, L. fermentum, L. brevis, L. buchneri;* Lactic acid streptococci, e.g. *Streptococcus lactis, Str. cremoris, Str. diacetylactis, Pediococcus pentosaceus, P. cerevisiae, Leuconostoc gracile, L. cremoris;* Fungi such as *Aspergillus sojae, A. oryzae, A. awamori;* and Yeast, such as *Saccharomyces rouxii, S. cerevisiae,* as well as combinations of the above-mentioned microorganisms.

The yeast extract obtained in accordance with the present invention without addition of extra RNA, typically comprises:
- 20-84% by weight of protein material (4-74% by weight of peptides and 5-80% by weight of free amino acids);
- 0.1-15, preferably 1-8% by weight of guanosine-5'-monophosphate; all calculated on dry extract.

Once enzymatic degradation and, if desired, fermentation have been carried out, the enzymatic and microbial activity in the enzymatically degraded mixture is inactivated. Further downstream processing of the resulting product is recommendable, such as removal of insoluble material (filtration or centrifuging), concentration (evaporation of water, spray-drying, oven drying, drum drying or freeze-drying, optionally in the presence of a suitable carrier like maltodextrin). Any sequence is feasible.

The food flavour thus obtained can be used per se to impart or reinforce the flavour of foodstuffs, optionally in combination with other flavouring materials. The admixture may result from physical mixing or chemical reaction to form reaction flavours.

The invention also comprises the yeast extract prepared by the process described above.

One embodiment of the present invention is therefore a method for flavouring food compositions by incorporating in the food composition a flavour as disclosed hereinbefore. More in particular the flavour -material is used to improve the flavour of soups, meat products, instant gravies, margarine, frying fat, drinks, bakery products, cheese, confectionary products and the like. The amount of flavour used in the food compositions varies widely but usually ranges between 0.1 and 10% (calculated as dry yeast extract flavour on the food composition ready for consumption). Preferably these amounts lie between 0.15 and 5%.

Comparative Example I 300 g of a yeast suspension, obtained by heating 220 g of baker's yeast (Saccharomyces cerevisiae strain yUR 470094, deposited at the Centaal bureau voor Schimmelcultures, P.O. Box 273, 3740 AG Baarn, Netherlands on 10 April 1989 under number CBS 270.89 having a dry matter content of 30%) in 80 g of water at about 100° C. for 30 min. at pH 6 and cooling to 65° C., was mixed with 30 g of a malt rootlets suspension, obtained by heating 2.7 g (milled) malt rootlets (ex Export Mouterij "Nederland", Wageningen, The Netherlands, dry matter content of 94%) in 27 g of water containing 24 mg of zinc acetate, and 109 mg papain (ex Merck & Co., Darmstadt, Germany, with an activity of 30,000 USP-U/mg). The mixture was thoroughly flushed with helium and subsequently heated for 18 hours at 65° C. at pH 5.6. The mixture was filtered. The product was obtained by evaporation of the filtrate in 61% yield containing 1.82% by weight 5'-GMP.

Example 1

300 g of a yeast suspension, obtained by heating 220 g of baker's yeast (*Saccharomyces cerevisiae* yUR 470094 having a dry matter content of 30%) in 80 g of water at about 100° C. for 30 min. at pH 6 and cooling to 65° C., was mixed with 30 g of a malt rootlets suspension, obtained by heating 2.7 g (milled) malt rootlets (ex Export Mouterij "Nederland", Wageningen, The Netherlands, dry matter content of 94%) in 27 g of water containing 24 mg of zinc acetate, and 109 mg papain (ex Merck & Co., Darmstadt, Germany, with an activity of 30,000 USP-U/mg). The mixture was saturated with oxygen. Subsequently, the mixture was heated for 18 hours at 65°° C. at pH 5.6. The mixture was filtered. The product was obtained by evaporation of the filtrate containing 3.90% by weight 5'-GMP, yeast extract yield: 46% by weight.

Example 2

300 g of a yeast suspension, obtained by heating 220 g of baker's yeast (*Saccharomyces cerevisiae* yUR 470094, having a dry matter content of 30%) in 80 g of water at about 100° C. for 30 min. at pH 6 and cooling to 65° C., was mixed with 30 g of a malt rootlets suspension, obtained by heating 2.7 g (milled) malt rootlets (ex Export Mouterij "Nederland", Wageningen, The Netherlands, dry matter content of 94%) in 27 g of water containing 24 mg of zinc acetate, and 109 mg papain (ex Merck & Co., Darmstadt, Germany, with an activity of 30,000 USP-U/mg). The mixture was thoroughly flushed with helium and subsequently heated for 6 hours at 65° C. at pH 5.6. Subsequently, the mixture was flushed with oxygen and allowed to react another 12 hours at 65° C. The mixture was filtered. The product was obtained by evaporation of the filtrate containing 3.2% by weight 5'-GMP, yeast extract yield: 59% by weight.

Figure 2:
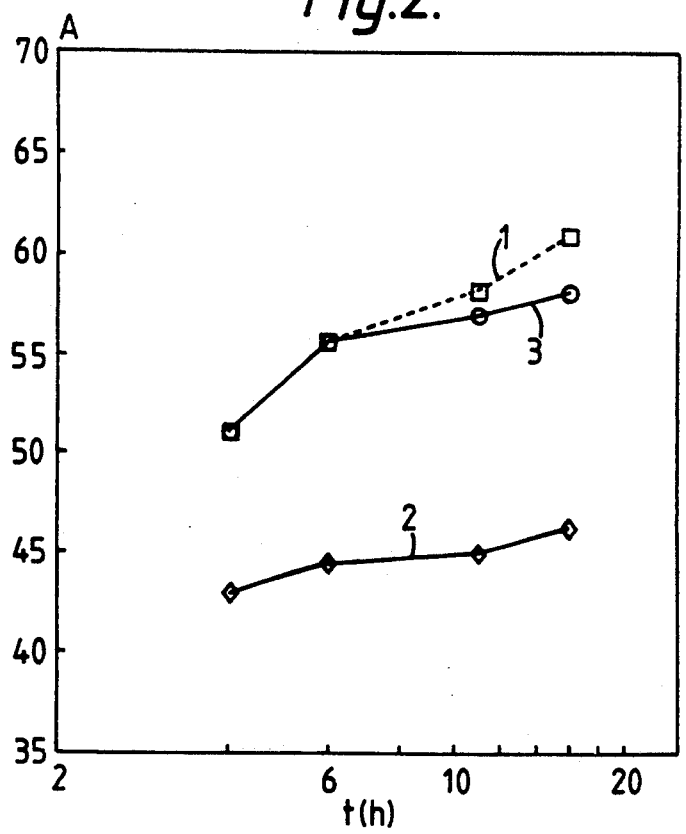

FIGS. 1 and 2 show the influence of the oxidizing conditions as a function of time (hours) on the 5'-GMP yield (B; FIG. 1, yield (percentage) w.w. on starting yeast dry matter) and yeast extract yield (percentage w.w.) (A; FIG. 2).

FIG. 1 shows that under oxidizing conditions (line 2) the 5'-GMP yield is much higher than under anaerobic conditions (line 1). But the 5'-GMP yield is drastically increased when, after some time (6 hours), the anaerobic degradation conditions are changed into oxidizing degradation conditions. Within about 5 hours the 5'-GMP yield has reached the 5'-GMP yield obtainable under only oxidizing conditions.

FIG. 2 shows that the yeast extract yield is appreciably lower under oxidizing conditions (line 2) in comparison with anaerobic conditions (line 1), whereas a change from anaerobic to oxidizing conditions results in a relatively small lowering of the yeast extract yield.

Figure 3:
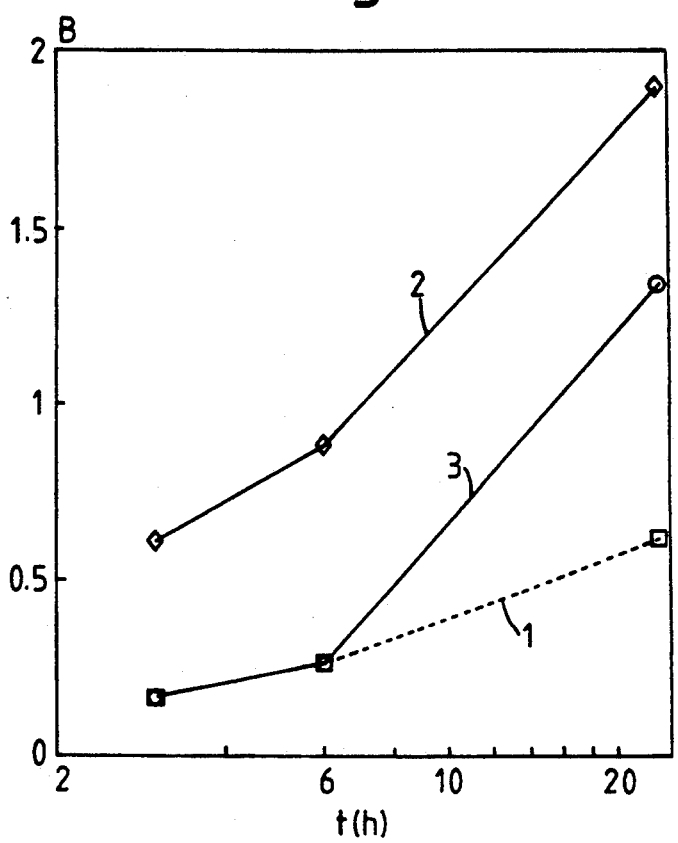
Figure 4:
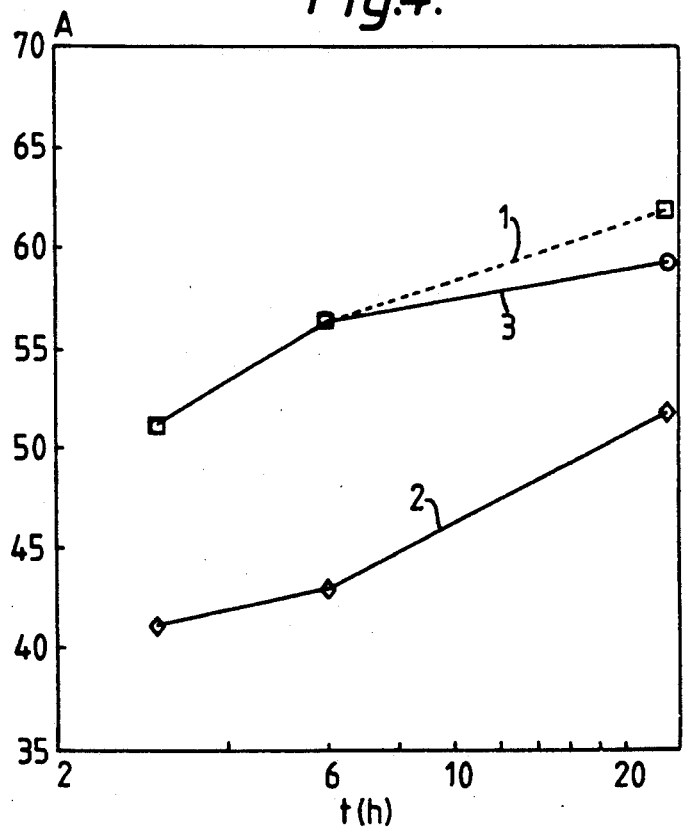

Comparative Example II 300 g of a yeast suspension, obtained by heating 220 g of commercially available baker's yeast (*Saccharomyces cerevisiae*, having a dry matter content of 30%) in 80 g of water at about 100° C. for 30 minutes at pH 6, was cooled to 65° C. and mixed with 100 mg of the phosphodiesterase-containing enzyme preparation ENZYME RP-1 (ex Amano Pharmaceutical Co., Japan; this enzyme preparation is manufactured by a fermentation process of a selected strain belonging to *Penicillium citrinum*) and 109 mg papain (ex Merck & Co., Darmstadt, Germany, with an activity of 30,000 USP-U/mg). The mixture was thoroughly flushed with pure nitrogen and heated for 24 hours at 65° C. and pH 5.6. After 3, 6 and 24 hours the amount of liberated 5'-GMP and the process yield were analysed (FIGS. 3 and 4, lines 1). The mixture was filtered after 24 hours. The product was obtained by evaporation of the filtrate containing 1.02% by weight of 5'-GMP; yeast extract yield: 62% by weight.

Example 3

300 g of a yeast suspension, obtained by heating 220 g of commercially available baker's yeast (*Saccharomyces cerevisiae*), having a dry matter content of 30%) in 80 g of water at about 100° C. for 30 minutes at pH 6, was cooled to 65° C. and mixed with 100 mg of the phosphodiesterase-containing enzyme preparation ENZYME RP-1 (ex Amano Pharmaceutical Co., Japan; this enzyme preparation is manufactured by a fermentation process of a selected strain belonging to *Penicillium citrinum*) and 109 mg papain (ex Merck & Co., Darmstadt, Germany, with an activity of 30,000 USP-U/mg). The mixture was thoroughly flushed with oxygen and heated for 24 hours at 65° C. and pH 5.6. After 3, 6 and 24 hours the amount of liberated 5'-GMP and the process yield were analysed (FIGS. 3 and 4, lines 2). The mixture was filtered after 24 hours. The product was obtained by evaporation of the filtrate containing 3.66% of 5'-GMP; yeast extract yield 52% by weight.

Example 4

300 g of a yeast suspension, obtained by heating 220 g of commercially available baker's yeast (*Saccharomyces cerevisiae*), having a dry matter content of 30%) in 80 g of water at about 100° C. for 30 minutes at pH 6, was cooled to 65° C. and mixed with 100 mg of the phosphodiesterase-containing enzyme preparation ENZYME RP-1 (ex Amano Pharmaceutical Co., Japan; this enzyme preparation is manufactured by a fermentation process of a selected strain belonging to Penicillium citrinum) and 109 mg papain (ex Merck & Co., Darmstadt, Germany, with an activity of 30,000 USP-U/mg). The mixture was thoroughly flushed with pure nitrogen and heated for 6 hours at 65° C. and pH 5.6. Subsequently the mixture was flushed with oxygen and allowed to react for another 18 hours at 65° C. After 3, 6 and 24 hours the amount of liberated 5'-GMP and the process yield were analysed (FIGS. 3 and 4, lines 3). The mixture was filtered after 24 hours. The product was obtained by evaporation of the filtrate containing 2.27% of 5'-GMP; yeast extract yield 59%.

Example 5

300 g of a yeast suspension, obtained by heating 220 g of baker's yeast (*Saccharomyces cerevisiae* yUR 470094, having a dry matter content of 30%) in 80 g of water at pH 5.9, was heated at 65° C. for 7 hours in the presence of 22.5 rag of papain (ex Merck & Co., Darmstadt, Germany, with an activity of 30,000 USP-U/mg). Subsequently the mixture was heated to 80°-100° C. for 30 minutes. After cooling to 65° C., 30 g of a malt rootlets suspension, obtained by heating 2.7 g (milled) malt rootlets (ex Export Mouterij "Nederland", Wageningen, The Netherlands, dry matter content of 94%) in 27 g of water containing 24 mg of zinc acetate was added. The mixture obtained was saturated with oxygen and heated for 12 hours at 65° C. The mixture was filtered. The product was obtained by evaporation of the filtrate in 55% yeast extract yield containing 3.4% 5'-GMP.

Example 6

300 g of a yeast suspension, obtained by heating 220 g of baker's yeast (*Saccharomyces cerevisiae* yUR 470094, having a dry matter content of 30%) in 80 g of water at pH 5.9, was heated at 57° C. for 7 hours in the presence of 22.5 mg of papain (ex Merck & Co., Darmstadt, Germany, with an activity of 30,000 USP-U/mg). Subsequently the mixture was heated to 80°-100° C. for 30 minutes. After cooling to 65° C., 30 g of a malt rootlets suspension, obtained by heating 2.7 g (milled) malt rootlets (ex Export Mouterij "Nederland", Wageningen, The Netherlands, dry matter content of 94%) in 27 g of water containing 24 mg of zinc acetate was added. The mixture obtained was saturated with oxygen and heated for 12 hours at 65° C. The temperature of the mixture was lowered to 55° C. 33 mg of Adenyl deaminase (Deamizyme "Amano" ex Amano Pharmaceutical Co. Ltd, Japan) was added, and the mixture was subsequently stirred for 2 hours. The mixture was filtered. The product was obtained by evaporation of the filtrate in 62% yeast extract yield, containing 3.3% 5'-IMP and 3.3% 5'-GMP.

It will be apparent that the ratio of the duration of the anaerobic and oxidizing conditions during the yeast degradation provides yeast extracts of a predeterminable 5'-GNP content and yeast extract yield.

The yeast extracts prepared according to the present invention may be used for preparing food compositions as disclosed in European patent application (EP-A) 191 513, however, leading to compositions with an improved savoury flavour.

We claim:

1. A method for the preparation of a yeast extract by degrading yeast with enzymes having RNA degrading activity yielding to 5'-ribonucleotides, wherein oxidizing conditions are maintained during the enzymatic degradation and the oxidizing conditions comprise an oxygen concentration of about 0.1 to 30 mg/l of aqueous yeast-containing medium.

2. The method as claimed in claim 1, wherein the yeast is degraded with enzymes having proteolytic activity and RNA degrading activity leading to 5'-ribonucleotides, and wherein the enzymatic degradation at least partly is carried out under oxidizing conditions.

3. The method as claimed in claim 2, wherein the proteolytic degradation is carried out under anaerobic conditions, and the RNA degrading activity leading to 5'-ribonucleotides under oxidizing conditions.

4. The method as claimed in claim 1, wherein the oxidizing conditions are selected dependent on a desired guanosine-5'-monophosphate (5'-GMP) content in the yeast extract.

5. The method as claimed in claim 1, wherein the oxidizing conditions are due to an oxidizing agent.

6. The method as claimed in claim 1, wherein a phosphodiesterase is used for the RNA degradation leading to 5'-ribonucleotides.

7. The method as claimed in claim 1 wherein endogenous yeast enzymes are inactivated prior to the RNA degradation leading to 5'-ribunocleotides.

8. The method as claimed in claim 1, wherein during or after the RNA degradation the yeast is also treated with enzymes having deaminase activity.

9. The method as claimed in claim 1, wherein the yeast is treated enzymatically with enzymes exhibiting cell-wall degrading activity, amylase, glycogen degrading activity, or lipolytic activity.

10. The method as claimed in claim wherein enzymatically degraded yeast is subjected to fermentation with micro-organisms.

11. Yeast extract obtained by degrading yeast with enzymes having RNA degrading activity leading to 5'-ribonucleotides wherein oxidizing conditions are maintained during the enzymatic degradation.

12. Flavouring composition comprising the yeast extract according to claim 11.

13. Food composition comprising the yeast extract of claim 11.

* * * * *